United States Patent
Kroon et al.

(10) Patent No.: US 11,020,093 B2
(45) Date of Patent: Jun. 1, 2021

(54) METHOD AND APPARATUS FOR IMPROVING THE MEASUREMENT OF FLOW VELOCITY OF BLOOD

(71) Applicant: KONINKLIJKE PHILIPS N.V., Eindhoven (NL)

(72) Inventors: Bart Kroon, Eindhoven (NL); Rick Bezemer, Amsterdam (NL); Denny Mathew, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 310 days.

(21) Appl. No.: 16/082,305

(22) PCT Filed: Mar. 23, 2017

(86) PCT No.: PCT/EP2017/056951
§ 371 (c)(1),
(2) Date: Sep. 5, 2018

(87) PCT Pub. No.: WO2017/162802
PCT Pub. Date: Sep. 28, 2017

(65) Prior Publication Data
US 2019/0090852 A1  Mar. 28, 2019

(30) Foreign Application Priority Data
Mar. 23, 2016  (EP) .................................... 16162037

(51) Int. Cl.
*A61B 8/08*  (2006.01)
*A61B 8/06*  (2006.01)
*A61B 8/00*  (2006.01)

(52) U.S. Cl.
CPC .............. *A61B 8/488* (2013.01); *A61B 8/065* (2013.01); *A61B 8/4245* (2013.01); *A61B 8/5215* (2013.01)

(58) Field of Classification Search
CPC ....... A61B 8/065; A61B 8/4245; A61B 8/488; A61B 8/5215; G16H 50/20
See application file for complete search history.

(56) References Cited

U.S. PATENT DOCUMENTS

| 4,509,526 A | 4/1985 | Barnes |
| 4,796,634 A | 1/1989 | Huntsman |
| (Continued) | | |

FOREIGN PATENT DOCUMENTS

| GB | 2257254 | 1/1993 |
| WO | 1999066835 | 12/1999 |
| (Continued) | | |

OTHER PUBLICATIONS

Jørgen Arendt Jensen "Linear description of ultrasound imaging systems"; Technical University of Denmark, Jun. 10, 1999.
(Continued)

*Primary Examiner* — Joanne M Hoffman
*Assistant Examiner* — Alexei Bykhovski

(57) ABSTRACT

There is provided a method of improving a measurement of the flow velocity of blood in a blood vessel of a subject, the method comprising using an ultrasound transducer to emit an ultrasound beam to measure flow velocity in a part of a body of a subject; forming a spatial time velocity profile for the part of the body from the measured flow velocity; and analyzing the spatial time velocity profile to determine a correction to the angle of the ultrasound beam with respect to the subject, the correction being based on a difference between the position of a peak in the spatial time velocity profile and the center of the spatial time velocity profile.

14 Claims, 5 Drawing Sheets

(56) References Cited

U.S. PATENT DOCUMENTS

| | | | |
|---|---|---|---|
| 5,052,395 A | 10/1991 | Burton | |
| 5,406,948 A | 4/1995 | Skidmore | |
| 5,409,010 A | 4/1995 | Beach | |
| 5,575,289 A | 11/1996 | Skidmore | |
| 5,928,153 A | 7/1999 | Chiang | |
| 6,261,233 B1 | 7/2001 | Kantorovich | |
| 6,565,513 B1 | 5/2003 | Phillips | |
| 8,473,239 B2 | 6/2013 | Specht | |
| 2005/0159664 A1 | 7/2005 | Phillips | |
| 2009/0292208 A1 | 11/2009 | Jeffrey | |
| 2013/0345566 A1* | 12/2013 | Weitzel | A61B 8/488 600/445 |
| 2014/0276072 A1 | 9/2014 | Martins | |

FOREIGN PATENT DOCUMENTS

| | | |
|---|---|---|
| WO | 2004004557 | 1/2004 |
| WO | 2004004559 | 1/2004 |
| WO | 2004012618 | 2/2004 |
| WO | 2004064631 | 8/2004 |
| WO | 2004064642 | 8/2004 |
| WO | 2004084735 | 10/2004 |
| WO | 2006024088 | 3/2006 |
| WO | 2006096915 | 9/2006 |
| WO | 2007134394 | 11/2007 |
| WO | 2014107769 | 7/2014 |

OTHER PUBLICATIONS

Haugen, et al., "Blood Flow Velocity Profiles in the Aortic Annulus: A 3-Dimensional Freehand Color Flow Doppler Imaging Study"; Journal of the American Society of Echocardiography, vol. 15 No. 4, Apr. 2002.

Bercoff, et al., "Ultrafast Compound Doppler Imaging: Providing Full Blood Flow Characterization"; IEEE Transactions on Ultrasonics, Ferroelectrics, and Frequency Control, vol. 58, No. 1, Jan. 2011.

Snider, et al., "Suprasternal Notch Echocardiography: A Two-dimensional Technique for Evaluating Congenital Heart Disease"; vol. 63, No. 1, Jan. 1981.

Girish Shirali, "Early Experience with a Miniaturized Three-dimensional Matrix Transducer in Children"; US Cardiovascular Disease, 2006.

* cited by examiner

METHOD AND APPARATUS FOR IMPROVING THE MEASUREMENT OF FLOW VELOCITY OF BLOOD

CROSS REFERENCE TO RELATED APPLICATIONS

This application is the U.S. National Phase application under 35 U.S.C. § 371 of International Application No. PCT/EP2017/056951, filed Mar. 23, 2017, published as WO 2017/162802 on Sep. 28, 2017, which claims the benefit of European Patent Application Number 16162037.2 filed Mar. 23, 2016. These applications are hereby incorporated by reference herein.

TECHNICAL FIELD OF THE INVENTION

The invention relates to a method and apparatus for improving the measurement of flow velocity of blood, and in particular relates to improving measurements of the flow velocity of blood using an ultrasound transducer.

BACKGROUND OF THE INVENTION

Cardiac output is a measure of the amount of blood that is pumped out of the heart in one minute. Cardiac output is determined as stroke volume (i.e. the volume of blood pumped per beat of the heart) multiplied by the number of heart beats per minute (i.e. the heart rate). This parameter (particularly beat-to-beat cardiac output) is difficult to measure non-invasively. However, it is possible to measure cardiac output from the flow velocity of the blood (which can be obtained using ultrasound Doppler) and the cross-sectional area of the aorta.

GB 2257254 describes a method and apparatus for measuring the cross-sectional area of blood vessels and blood flow velocity (and hence cardiac output) using Doppler ultrasound. An ultrasound probe is directed downwardly via the suprasternal notch and Doppler signals from the moving blood in the aorta are detected. Signal processing means determine the Doppler power at successive ranges and the resulting power curve is correlated against stored curves representing a range of known aorta cross-sectional areas to find the closest fit.

Typically, to estimate cardiac output, the operator has to manually aim the probe at the center of the aorta, and the cross-sectional area of the aorta is estimated from the weight or length of a patient, or estimated according to other techniques, such as those described in GB 2257254. This approach of calculating cardiac output is unreliable due to difficulty in locating the aorta, and interpersonal variations, especially at young and old ages. Moreover, multiple measurements of the cardiac output from the same patient can be inconsistent since the measurement is sensitive to the positioning of the probe. Thus the accuracy of the conventional solutions very much depend on the skill of the operator to identify the ascending aorta and determine the correct position of the transducer.

SUMMARY OF THE INVENTION

There is therefore a need for a method and apparatus that can improve measurements of flow velocity and thus cardiac output.

According to a first aspect, there is provided method of improving a measurement of the flow velocity of blood in a blood vessel of a subject, the method comprising: using an ultrasound transducer to emit an ultrasound beam to measure flow velocity in a part of a body of a subject; forming a spatial time velocity profile for the part of the body from the measured flow velocity; and analyzing the spatial time velocity profile to determine a correction to the angle of the ultrasound beam with respect to the subject, the correction being based on a difference between the position of a peak in the spatial time velocity profile and the center of the spatial time velocity profile. Therefore, the method determines how the angle of the ultrasound beam should be corrected in order to center a flow velocity peak and thus improve a measurement of flow velocity.

In some embodiments, the peak in the spatial time velocity profile comprises the maximum flow velocity in the spatial time velocity profile.

In some embodiments, the method further comprises the step of providing feedback to an operator of the ultrasound transducer based on the determined correction to the angle. The feedback to the operator can comprise an indication of a rotation of the ultrasound transducer with respect to the subject that would position the peak in the spatial time velocity profile in, or nearer to, the center of the spatial time velocity profile. The indication can be a visual, aural and/or tactile indication, or a combination thereof. This embodiment has an advantage that the operator can be guided as to an improved or correct positioning of the ultrasound transducer with respect to the subject.

In further or alternative embodiments, the method further comprises the steps of determining a first control signal for the ultrasound transducer based on the determined correction to the angle; and adjusting the direction of the ultrasound beam emitted by the ultrasound transducer according to the determined first control signal such that the position of the peak in the spatial time velocity profile is in, or nearer to, the center of the spatial time velocity profile. This embodiment has an advantage that the angle of the ultrasound beam can be automatically adjusted to improve the flow velocity measurement without requiring the use of an actuator.

In further or alternative embodiments, the method further comprises the step of determining a second control signal for an orientation actuator for the ultrasound transducer based on the determined correction to the angle, wherein the orientation actuator is capable of adjusting the orientation of the ultrasound transducer with respect to the subject. In these embodiments, the method can further comprise the step of controlling the orientation actuator using the second control signal to adjust the orientation of the ultrasound transducer with respect to the subject such that the position of the peak in the spatial time velocity profile would be in, or nearer to, the center of the spatial time velocity profile. This embodiment has an advantage that the angle of the ultrasound beam can be automatically adjusted to improve the flow velocity measurement.

In further or alternative embodiments, the method further comprises the step of determining a correction to a value of a flow velocity in the spatial time velocity profile based on the determined correction to the angle.

In some embodiments, the step of using an ultrasound transducer comprises using the ultrasound transducer to measure flow velocity at a plurality of depths in the part of the body; the step of forming a spatial time velocity profile comprises forming a respective spatial time velocity profile for each of the plurality of depths, each spatial time velocity profile being formed from the measured flow velocity at the respective depth; and the step of analyzing the spatial time velocity profile to determine a correction to the angle of the ultrasound beam comprises analyzing one or more of the plurality of spatial time velocity profiles to determine the correction to the angle of the ultrasound beam.

In some embodiments, the method further comprises the step of analyzing the spatial time velocity profiles to determine a correction to the position of the ultrasound transducer with respect to the subject, In some embodiments, the step of analyzing the spatial time velocity profiles to determine a correction to the position of the ultrasound transducer with respect to the subject, comprises determining the correction based on the fitting of a geometric model of the arterial path through peaks in the spatial time velocity profiles.

In some embodiments, the method further comprises the step of providing feedback to an operator of the ultrasound transducer based on the determined correction to the position. The feedback to the operator can comprise an indication of a movement of the ultrasound transducer with respect to the subject that would improve the alignment of the ultrasound transducer with the artery. The indication can be a visual, aural and/or tactile indication, or a combination thereof. This embodiment has an advantage that the operator can be guided as to an improved or correct positioning of the ultrasound transducer with respect to the subject.

In further or alternative embodiments, the method further comprises the step of determining a third control signal for a position actuator for the ultrasound transducer based on the determined correction to the position, wherein the position actuator is capable of adjusting the position of the ultrasound transducer with respect to the subject. The method can further comprise the step of controlling the position actuator using the third control signal to adjust the position of the ultrasound transducer with respect to the subject such that the alignment of the ultrasound transducer with the artery is improved. This embodiment has an advantage that the position of the ultrasound beam can be automatically adjusted to improve the flow velocity measurement.

According to a second aspect, there is provided a computer program product comprising a computer readable medium having computer readable code embodied therein, the computer readable code being configured such that, on execution by a suitable computer, control unit or processor, the computer, control unit or processor is caused to control an ultrasound transducer connected to the computer, control unit or processor to emit an ultrasound beam to measure flow velocity in a part of a body of a subject; form a spatial time velocity profile for the part of the body from the measured flow velocity; and analyze the spatial time velocity profile to determine a correction to the angle of the ultrasound beam with respect to the subject, the correction being based on a difference between the position of a peak in the spatial time velocity profile and the center of the spatial time velocity profile.

More generally, the computer readable code according to the second aspect is configured such that a suitable computer, control unit or processor is caused to perform any of the methods described above.

According to a third aspect, there is provided an apparatus for measuring flow velocity of blood in a blood vessel of a subject, the apparatus comprising a control unit that is configured to obtain measurements of flow velocity in a part of a body of a subject, wherein the measurements are made using an ultrasound transducer that emits an ultrasound beam; form a spatial time velocity profile for the part of the body from the measured flow velocity; and analyze the spatial time velocity profile to determine a correction to the angle of the ultrasound beam with respect to the subject, the correction being based on a difference between the position of a peak in the spatial time velocity profile and the center of the spatial time velocity profile. Therefore, the apparatus determines how the angle of the ultrasound beam should be corrected in order to center a flow velocity peak and thus improve a measurement of flow velocity.

In some embodiments, the apparatus further comprises an ultrasound transducer.

In some embodiments, the peak in the spatial time velocity profile comprises the maximum flow velocity in the spatial time velocity profile.

In some embodiments, the control unit is further configured to determine feedback for an operator of the ultrasound transducer based on the determined correction to the angle. The feedback to the operator can comprise an indication of a rotation of the ultrasound transducer with respect to the subject that would position the peak in the spatial time velocity profile in, or nearer to, the center of the spatial time velocity profile. The indication can be a visual, aural and/or tactile indication, or a combination thereof. In some embodiments, the apparatus can further comprise a user interface component for providing the determined feedback to the operator. This embodiment has an advantage that the operator can be guided as to an improved or correct positioning of the ultrasound transducer with respect to the subject.

In further or alternative embodiments, the control unit is further configured to determine a first control signal for the ultrasound transducer based on the determined correction to the angle; and output the first control signal for adjusting the direction of the ultrasound beam emitted by the ultrasound transducer such that the position of the peak in the spatial time velocity profile is in, or nearer to, the center of the spatial time velocity profile. This embodiment has an advantage that the angle of the ultrasound beam can be automatically adjusted to improve the flow velocity measurement without requiring the use of an actuator.

In further or alternative embodiments, the control unit is further configured to determine a second control signal for an orientation actuator for the ultrasound transducer based on the determined correction to the angle, wherein the orientation actuator is capable of adjusting the orientation of the ultrasound transducer with respect to the subject. In these embodiments, the control unit is further configured to control the orientation actuator using the second control signal to adjust the orientation of the ultrasound transducer with respect to the subject such that the position of the peak in the spatial time velocity profile would be in, or nearer to, the center of the spatial time velocity profile. In some embodiments, the apparatus further comprises an orientation actuator that is configured to adjust the orientation of the ultrasound transducer with respect to the subject. This embodiment has an advantage that the angle of the ultrasound beam can be automatically adjusted to improve the flow velocity measurement.

In further or alternative embodiments, the control unit is further configured to determine a correction to a value of a flow velocity in the spatial time velocity profile based on the determined correction to the angle.

In some embodiments, the measurements of the flow velocity are indicative of flow velocity at a plurality of depths in the part of the body; and wherein the control unit is configured to form a respective spatial time velocity profile for each of the plurality of depths, each spatial time velocity profile being formed from the measured flow velocity at the respective depth; and the control unit is configured to analyze the spatial time velocity profile to determine a correction to the angle of the ultrasound beam by analyzing one or more of the plurality of spatial time velocity profiles to determine a correction to the angle of the ultrasound beam.

In some embodiments, the control unit is further configured to analyze the spatial time velocity profiles to determine a correction to the position of the ultrasound transducer with respect to the subject, In some embodiments, the control unit is configured to analyze the spatial time velocity profiles to determine a correction to the position of the ultrasound transducer with respect to the subject by determining the correction based on the fitting of a geometric model of the arterial path through peaks in the spatial time velocity profiles.

In some embodiments, the control unit is further configured to determine feedback for an operator of the ultrasound transducer based on the determined correction to the position. The feedback to the operator can comprise an indication of a movement of the ultrasound transducer with respect to the subject that would improve the alignment of the ultrasound transducer with the artery. The indication can be a visual, aural and/or tactile indication. In some embodiments, the apparatus can further comprise a user interface component for providing the determined feedback to the operator. This embodiment has an advantage that the operator can be guided as to an improved or correct positioning of the ultrasound transducer with respect to the subject.

In further or alternative embodiments, the control unit is further configured to determine a third control signal for a position actuator for the ultrasound transducer based on the determined correction to the position, wherein the position actuator is capable of adjusting the position of the ultrasound transducer with respect to the subject. In these embodiments, the control unit is further configured to control the position actuator using the third control signal to adjust the position of the ultrasound transducer with respect to the subject such that the alignment of the ultrasound transducer with the artery is improved. In some embodiments, the apparatus further comprises a position actuator that is capable of adjusting the position of the ultrasound transducer with respect to the subject. This embodiment has an advantage that the position of the ultrasound transducer can be automatically adjusted to improve the flow velocity measurement.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

The invention is for use in measuring the flow velocity of blood in a blood vessel, for example an artery or vein, particularly the ascending aorta or pulmonary artery, of a subject. The aorta is the main artery in the human body and starts at the left cardiac ventricle and extends down the chest and abdomen of the body. The ascending aorta is the part of the aorta extending out of the top of the left ventricle before the aorta curves downwards. The pulmonary artery is the artery that connects the right ventricle of the heart to the lungs. Although the following description of the invention refers to measuring the flow velocity of blood in an artery, it will be appreciated that the invention can also be used to measure flow velocity in veins.

In some embodiments, an ultrasound transducer can be used on, in or near the suprasternal notch of a subject in order to measure the flow velocity of blood in the ascending aorta. In other embodiments, an ultrasound transducer can be used in a parasternal position to measure the flow velocity of the blood in the pulmonary artery.

Figure 1:
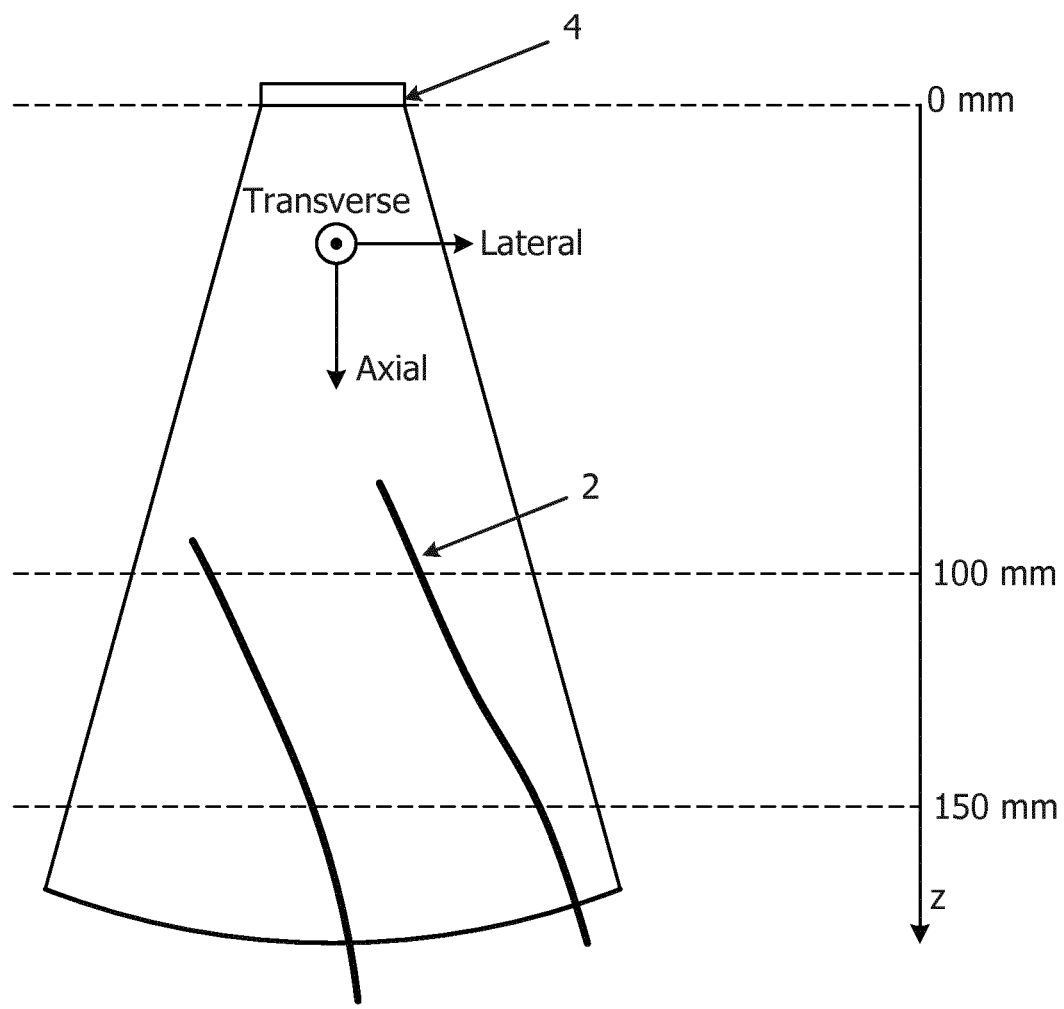
FIG. 1 is an illustration of the type of measurement performed using the invention.

FIG. 1 illustrates a measurement scenario in which the invention can be used. FIG. 1 shows an aorta 2 (ascending or pulmonary) which is oriented in a generally vertical direction with blood flowing upwards, and an ultrasound transducer 4 that is positioned above the aorta 2. In the following description of the invention, reference is made to transverse, lateral and axial directions relative to the transducer 4. These three directions are shown in FIG. 1, with the axial direction (also referred to as the z-axis) corresponding to the direction that is perpendicular to the plane of the transducer 4, and the transverse and lateral directions (also referred to the x- and y-axes) comprising orthogonal axes in the plane of the transducer 4.

The transducer 4 measures flow velocity in the axial direction across at least one cross-section using ultrasound Doppler techniques to form a spatial time velocity profile. FIG. 1 shows two exemplary cross-sections at a distance of 100 mm and 150 mm from the transducer 4 although these should not be considered to be limiting. At a depth of around 150 mm into the body the aorta 4 is generally aligned with the transducer 4.

Figure 2:
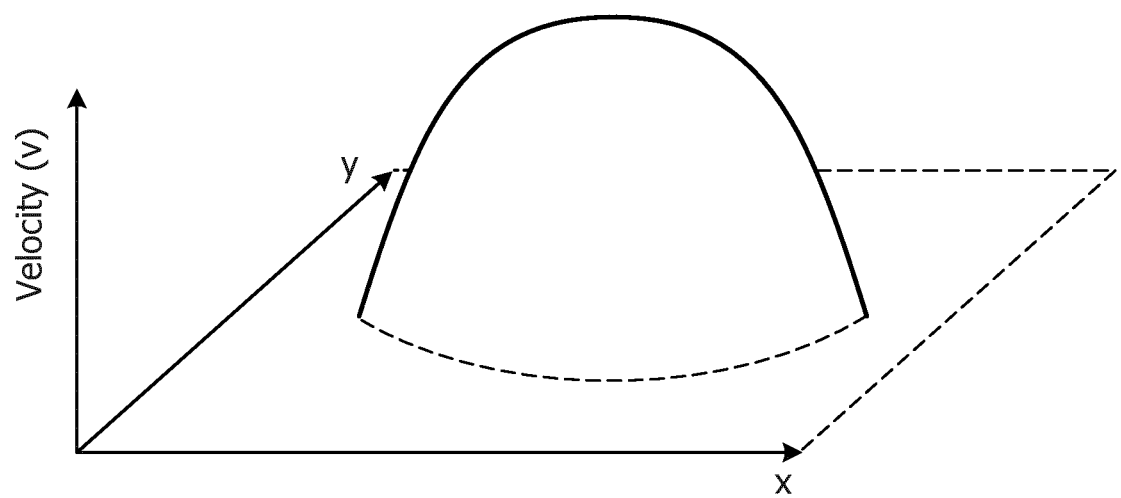
FIG. 2 is a diagram illustrating an exemplary spatial time velocity profile for an artery.

An exemplary arterial blood spatial time velocity profile (i.e. a spatial distribution of velocities) is shown in FIG. 2, and it can be seen that, as expected for a flow of viscous fluid through a tube, the velocity increases towards the center of the artery. Those skilled in the art will appreciate that a spatial time velocity profile comprises a velocity measurement or estimate at each of a plurality of positions on a two-dimensional plane/cross-section.

As noted above, to estimate cardiac output, an operator of an ultrasound probe has to manually aim the probe at the center of the aorta. However the accuracy of the flow velocity measurement is sensitive to the positioning of the probe. Therefore the invention aims to improve the accuracy of an ultrasound measurement of flow velocity by analyzing a spatial time velocity profile obtained by the ultrasound transducer and determining a correction to the angle of the ultrasound transducer with respect to the subject (which is also referred to herein as the orientation of the transducer). In some embodiments, spatial time velocity profiles for a plurality of depths can be analyzed in order to determine a correction to the angle and position of the ultrasound transducer.

In some embodiments, the determined correction can then be indicated to an operator in order for the operator to make an adjustment to the positioning of the ultrasound transducer, and/or an actuator can be controlled according to the determined correction to automatically adjust the positioning of the transducer.

Figure 3:
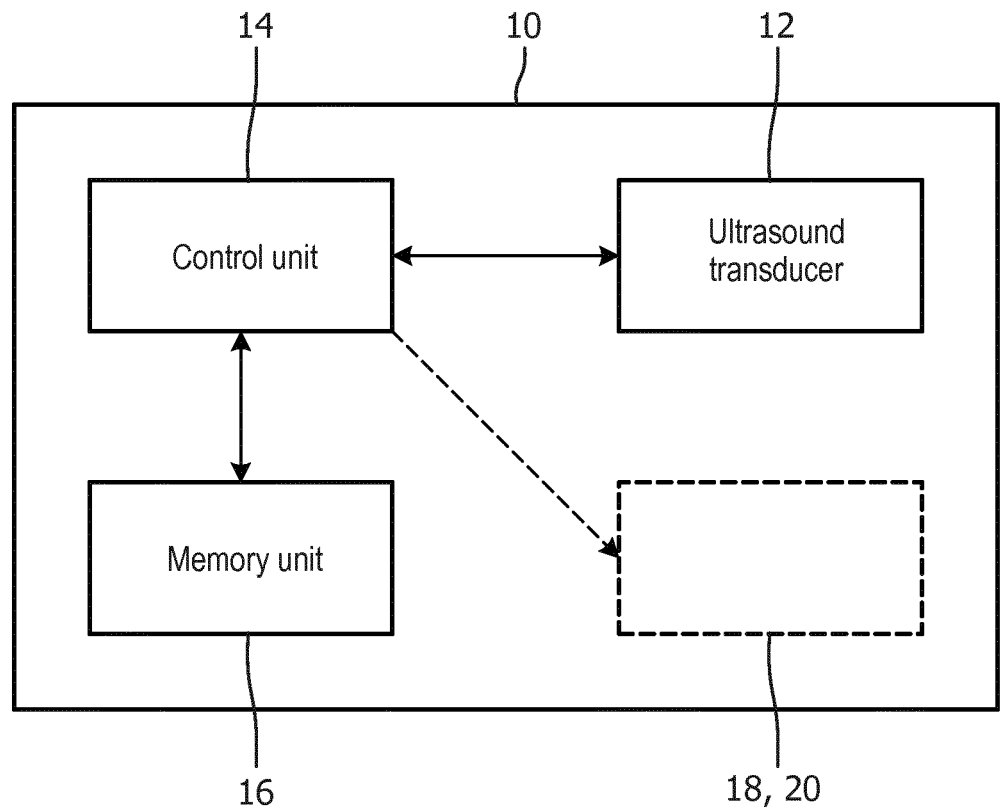
FIG. 3 is a block diagram of an apparatus according to an embodiment of the invention.

An exemplary apparatus for measuring the flow velocity of blood according to an embodiment of the invention is shown in FIG. 3. The apparatus 10 comprises an ultrasound transducer 12 that is for emitting ultrasound and measuring ultrasound reflections.

The ultrasound transducer 12 can comprise a plurality of transducer elements that generate ultrasound and measure the reflected ultrasound. The ultrasound transducer 12 can be a continuous-wave (CW) Doppler ultrasound transducer 12 or a pulsed-wave (PW) Doppler ultrasound transducer 12.

In some embodiments, the ultrasound transducer 12 can comprise a plurality of transducer elements arranged as a linear array of transducer elements, and the ultrasound transducer 12 can be provided with an acoustic lens or other acoustic beam shaping element in order to create an annulus-shaped or toroidal-shaped ultrasound beam. This ultrasound beam can be used to obtain spatial-time-velocity information from the subject (e.g. time-velocity information in the lateral and transverse directions).

In other embodiments, the ultrasound transducer 12 can comprise a plurality of transducer elements, and the transducer elements can be arranged in a two-dimensional (2D) array. The transducer elements can be driven individually or in combination in order to generate and steer an ultrasound beam and thereby obtain spatial-time-velocity information from the subject. This type of ultrasound transducer 12 can be used to obtain spatial-time-velocity information in a three-dimensional (3D) volume of the subject, and thus spatial-time-velocity information at a plurality of depths in the subject (e.g. time-velocity information in the lateral and transverse directions at a plurality of depths).

Those skilled in the art will be aware of suitable types of ultrasound transducer 12 that can be used in embodiments according to the invention.

The ultrasound transducer 12 is connected to a control unit 14 that controls the operation of the transducer 12 and that receives the output of the transducer 12. The ultrasound transducer 12 can output measurements of the received ultrasound reflections to the control unit 14, and the control unit 14 can analyze the Doppler shift in the ultrasound reflections to determine measurements of flow velocity. The control unit 14 can comprise one or more processors, processing units, multi-core processors or modules that are configured or programmed to control the apparatus 10 and components thereof to determine a measurement of flow velocity of blood in an artery of the subject as described below.

The apparatus 10 can also comprise a memory unit 16 that can be used for storing program code that can be executed by the control unit 14 to perform the method described herein. The memory unit 16 can also be used to store signals and measurements made or obtained by the apparatus 10 and/or by the ultrasound transducer 12.

In some embodiments, the apparatus 10 can further comprise a user interface 18 for providing feedback to the operator of the apparatus 10 and/or one or more actuators 20 for adjusting the angle (orientation) and/or position of the ultrasound transducer 12 with respect to the subject based on a control signal from the control unit 14.

The user interface 18 is to provide feedback to the operator to instruct, enable or encourage the operator to adjust the angle and/or position of the ultrasound transducer 12 in order to improve the accuracy and/or reliability of the measurement of flow velocity. The user interface 18 can therefore comprise any component that is suitable for providing this feedback/information, and can be, for example, any one or more of a display screen or other visual indicator, a speaker, one or more lights, and a component for providing tactile feedback (e.g. a vibration function). In addition to providing the above feedback, the user interface 18 can be used to provide the subject or operator of the apparatus 10 (for example a healthcare provider) with information resulting from the method according to the invention. For example the user interface 18 can provide an indication of the flow velocity of the subject.

The one or more actuators 20 can comprise any suitable means for enabling the angle and/or position of the ultrasound transducer 12 to be adjusted with respect to the subject. The one or more actuators 20 can be any type of actuator 20 that is capable of moving or controlling a mechanism or system to change the orientation and/or position of the ultrasound transducer 12. The actuator can be based on electric, magnetic, pneumatic or hydraulic principles, or any combination thereof. The most suitable types of actuator are electric or magnetic actuators. An electric actuator can be a motor or piezoelectric component. A magnetic actuator can be actuated by applying magnetic energy. These types of actuators are typically compact, lightweight, economical, and with high power density. Magnetic actuators can use shape memory materials (SMMs), such as shape memory alloys (SMAs), or magnetic shape-memory alloys (MSMAs). One suitable type of actuator are electroactive polymers (EAPs), which are polymers that exhibit a change in size or shape when stimulated by an electric field. EAPs can have several configurations, but are generally divided in two principal classes: dielectric and ionic.

In some embodiments (which can be separate or combined with those set out above), adjustment of the ultrasound transducer 12 can be effected by adjusting the direction of an ultrasound beam from the ultrasound transducer 12, for example by adjusting the phase of individual transducer array elements in the ultrasound transducer 12.

It will be appreciated that FIG. 3 only shows the components required to illustrate this aspect of the invention, and in a practical implementation the apparatus 10 will comprise additional components to those shown. For example, the apparatus 10 may comprise a battery or other power supply for powering the apparatus 10 or means for connecting the apparatus 10 to a mains power supply, and/or a communication module for enabling the flow velocity measurements to be communicated to a remote computer.

Figure 4A:
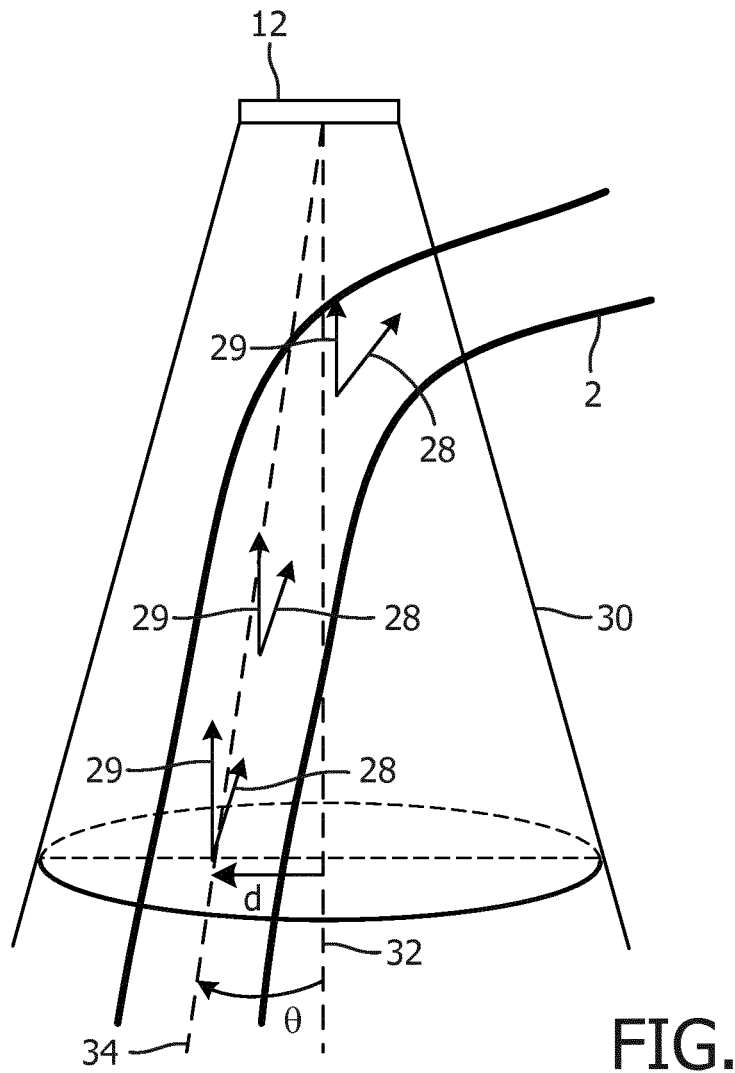
FIG. 4 illustrates a scenario in which the invention can be used.
Figure 4B:
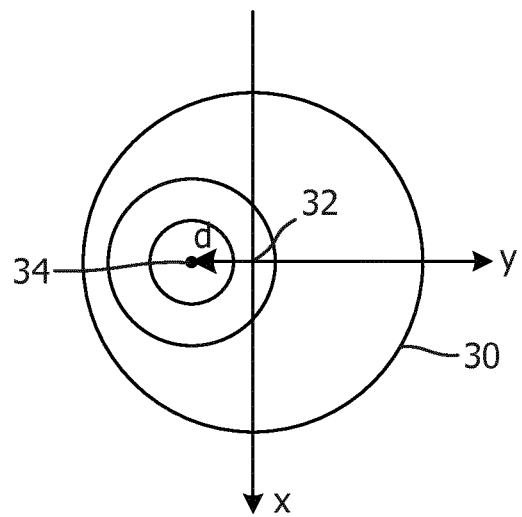
Figure 5:
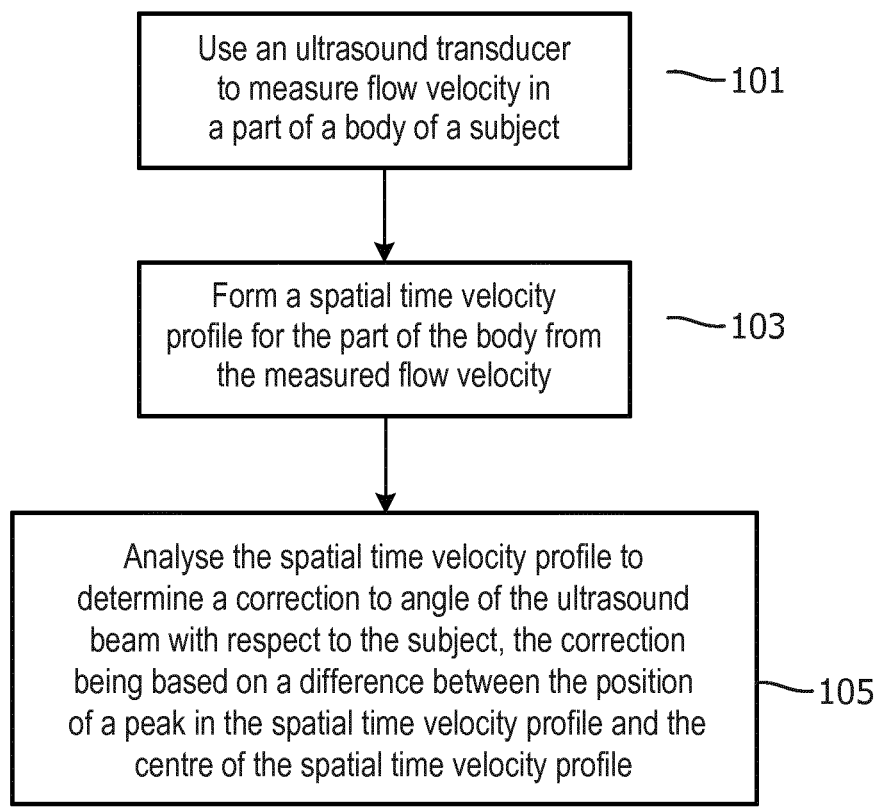
FIG. 5 is a flow chart illustrating a method of improving measurements of flow velocity of blood according to an embodiment.

FIG. 4 illustrates a scenario in which the invention can be used, and FIG. 5 is a flow chart illustrating a method according to an embodiment.

FIG. 4(a) shows an aorta 2 and an ultrasound transducer 12 that is positioned generally above the aorta 2 (for example in the suprasternal notch of the subject). Vectors 28 indicate the direction of blood flow in the aorta 2, and vectors 29 indicate the component of the velocity towards the ultrasound transducer 12 that can be measured by ultrasound transducer 12. In this embodiment the ultrasound transducer 12 may not have the ability to obtain spatial-time-velocity information at a plurality of depths, and thus the spatial-time-velocity profile is obtained by integrating the axial component of the velocity of the blood flow at all depths for each (2D) spatial position. The ultrasound beam 30 from the ultrasound transducer 12 is shown in FIG. 4(a), and in this illustration, the ultrasound transducer 12 is not correctly aligned with the aorta 2 (as shown by the center axis 32 of the ultrasound beam being offset by an angle θ from the axis 34 of the aorta 2).

FIG. 4(b) shows a spatial-time-velocity profile obtained using the ultrasound transducer 12 where the center axis 32 of the ultrasound beam is offset by an angle θ from the axis 34 of the aorta 2, and it can be seen that the center of the part of the spatial-time-velocity profile relating to the flow of blood in the aorta 2 is offset from the center axis 32 of the ultrasound beam 30 by a distance d. This offset leads to off-center angles interacting with the high-velocity center of the aorta 2, thereby 'smearing' the obtained spatial-time-velocity profile.

Where the ultrasound transducer 12 is not aligned with the aorta 2, the accuracy and repeatability of flow velocity measurements of the blood in the aorta 2 will be compromised. The method according to this embodiment of the invention therefore aims to detect this offset to enable an operator and/or the apparatus 10 to take corrective action.

Thus, in step 101, an ultrasound transducer 12 that emits an ultrasound beam is used to measure flow velocity in a part of a body of a subject. For example, the ultrasound transducer 12 can be used on, in or near the suprasternal notch of a subject in order to measure the flow velocity of blood in the ascending aorta. In other embodiments, an ultrasound transducer can be used in a parasternal position to measure the flow velocity of the blood in the pulmonary artery. In step 101, flow velocity is measured in a plurality of spatial directions. The ultrasound transducer 12 can measure the flow velocities at a particular depth, or the ultrasound transducer 12 can measure the flow velocities as the integral of the axial component of the velocity of the blood flow at all depths for each spatial position.

In step 103, a spatial time velocity profile (for example as shown in FIGS. 2 and 4(b)) is formed for the part of the body from the measured flow velocities. That is, a spatial time velocity profile indicating the flow velocity for each of a number of different positions in the lateral and transverse directions is formed from the flow velocity measurements made in a plurality of directions from the ultrasound transducer 12. Step 103 can be performed by control unit 14.

In step 105, the spatial time velocity profile is analyzed to determine a correction to the angle of the ultrasound beam emitted by ultrasound transducer 12 with respect to the subject. In particular, the spatial-time-velocity profile is analyzed to identify a peak in the profile, and the difference between the position of the peak in the spatial time velocity profile and the center of the spatial time velocity profile (corresponding to the intersection of the axis 32 in FIG. 4(a) with the profile) is determined. The correction to the angle of the ultrasound beam is based on the determined difference. Step 105 can be performed by control unit 14. The peak in the spatial time velocity profile identified in step 105 can be the maximum flow velocity in the spatial time velocity profile.

In some embodiments, the method further comprises the step of providing feedback to an operator of the ultrasound transducer based on the determined correction to the angle. The feedback can be provided in any suitable form using any suitable feedback means in user interface 18.

For example, in some embodiments, the feedback can simply comprise an indication that the orientation of the ultrasound transducer 12 is not correct, in which case the operator can adjust the orientation of the ultrasound transducer 12 until the feedback indicates that the orientation is correct (i.e. when the peak in the spatial time velocity profile is within a threshold distance of or is at the center of the spatial time velocity profile). The indication can be a visual, aural and/or tactile indication, or a combination thereof.

In other embodiments, the feedback can be an indication of the rotation of the ultrasound transducer 12 with respect to the subject and/or an indication of the direction of the rotation of the ultrasound transducer 12 that is required in order to position the peak in the time velocity profile in, or nearer to, the center of the spatial time velocity profile. The indication can be a visual, aural and/or tactile indication, or a combination thereof.

In some embodiments, which can be in addition to or alternatively to the embodiments in which feedback is provided to the operator, the method can further comprise determining a control signal (also referred to herein as a first control signal) for the ultrasound transducer 12 based on the determined correction to the angle that can be used to steer the ultrasound beam 30 produced by the ultrasound transducer 12. The ultrasound transducer 12 can then be controlled using the first control signal to adjust the direction in which the ultrasound beam 30 is emitted with respect to the subject such that the position of the peak in the time velocity profile is in, or nearer to, the center of the spatial time velocity profile. In particular, the first control signal can be used to adjust the phase of individual transducer elements in the ultrasound transducer 12 in order to steer the ultrasound beam 30 in the required direction.

In some embodiments, which can be in addition to or alternatively to the embodiments in which feedback is provided to the operator, the method can further comprise determining a control signal (also referred to herein as a second control signal) for an orientation actuator 20 for the ultrasound transducer 12 based on the determined correction to the angle. The orientation actuator 20 can then be controlled using the second control signal to adjust the orientation of the ultrasound transducer 12 with respect to the subject such that the position of the peak in the time velocity profile is in, or nearer to, the center of the spatial time velocity profile.

Once the orientation of the ultrasound transducer 12 has been adjusted, either by the operator in response to the operator feedback or by beam steering or by the orientation actuator 20, steps 101-105 can be repeated. If in step 105 it is determined that no correction is required to the angle of the ultrasound transducer 12, then the spatial time velocity profile determined in step 103 can be analyzed to determine the flow velocity of the blood in the aorta 2, and/or any other cardiac parameter that can be derived from the flow velocity of the blood, for example using an aortic flow model.

In some embodiments, the method can further comprise the step of determining a correction to a value of a flow velocity in the spatial time velocity profile based on the determined correction to the angle. This step can be performed in addition or alternatively to the providing feedback and determining control signal steps set out above. In particular, in this step information from the spatial time velocity profile can be used to estimate the residual angle error of the aorta 2 with respect to the ultrasound transducer 12, and the blood flow velocity estimate from the profile can be corrected using this residual angle error (for example by multiplying by the secant of the angle). Where this step is performed as an alternative to the providing feedback and determining control signal steps, this step has the advantage that an automatic 'correction' to the angle (or more directly the flow velocity itself) can be made without requiring the apparatus 10 to include an actuator 20.

In some embodiments, the ultrasound transducer 12 may be able to measure flow velocity at a plurality of depths so that spatial-time-velocity profiles can be determined for specific depths. In this case, the step of analyzing (step 105) can comprise analyzing one or more of the plurality of spatial time velocity profiles to determine a correction to the angle of the ultrasound beam. Where different corrections are determined from each spatial time velocity profile, the correction for one of them, or an average of the corrections, can be selected as the output of step 105.

Figure 6:
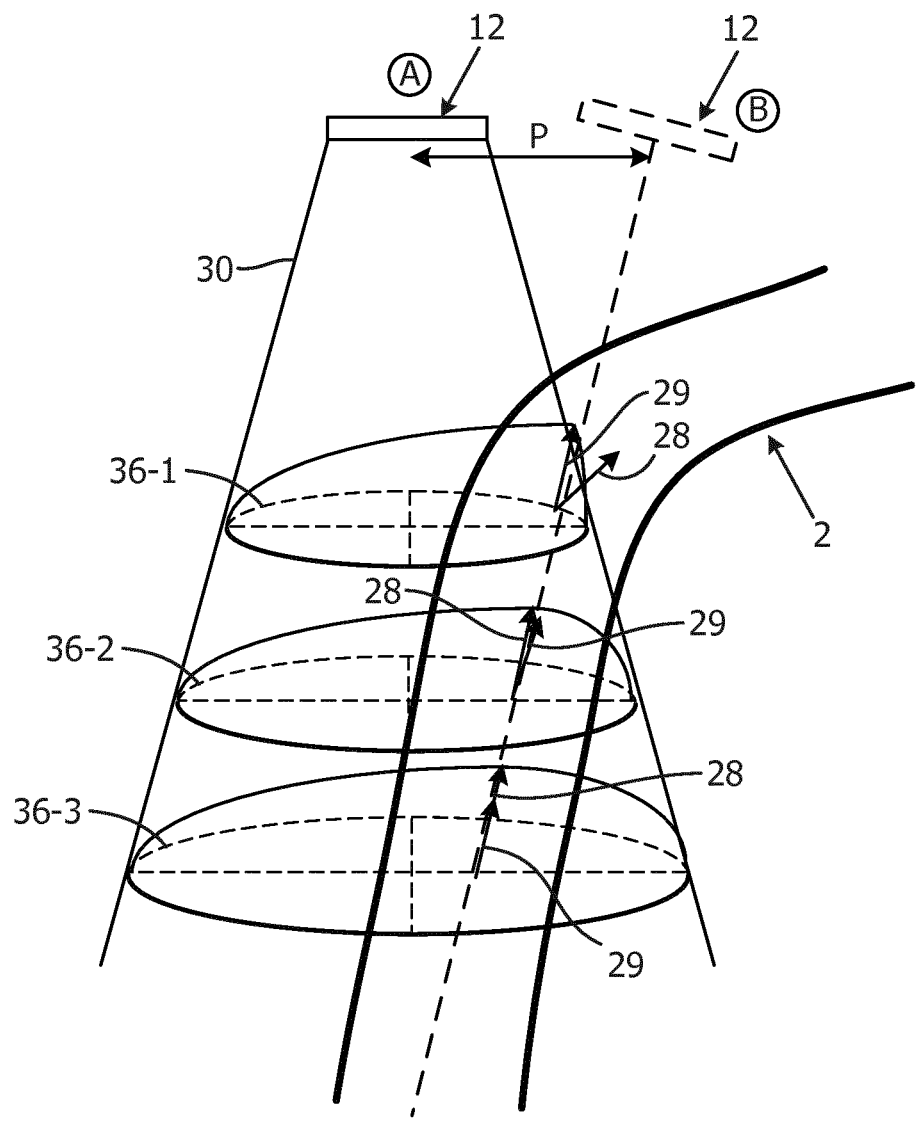
FIG. 6 illustrates another scenario in which the invention can be used.

FIG. 6 illustrates another scenario in which the invention can be used. FIG. 6 shows an aorta 2 and an ultrasound transducer 12 that is positioned in position A generally above the aorta 2 (for example in the suprasternal notch of the subject). Vectors 28 indicate the direction of blood flow in the aorta 2, and vectors 29 indicate the component of the velocity towards the ultrasound transducer 12 that can be measured by ultrasound transducer 12. In this embodiment the ultrasound transducer 12 can measure the spatial-time-velocity information individually at a plurality of depths (e.g. it can be a 3D ultrasound system), and thus separate spatial-time-velocity profiles are obtained. Three depths are shown in FIG. 6, and the resulting spatial-time-velocity profiles are shown in the figure (labelled 36-1, 36-2 and 36-3). The ultrasound beam 30 from the ultrasound transducer 12 is shown, and in this illustration, the ultrasound transducer 12 is not correctly positioned with respect to the aorta 2, as shown by the ultrasound transducer 12 being offset in the lateral and/or transverse directions by a distance P from an ideal measurement position B. It can be seen that in each of the profiles 36-1, 36-2 and 36-3, the peak in the flow velocity is offset from the center of the profile (with the peak being increasingly offset as the measurement depth decreases).

In this scenario, the method in FIG. 5 can be used to identify a correction to the angle of the ultrasound beam from the obtained spatial time velocity profiles. In addition, the spatial time velocity profiles can be analyzed to determine a correction to the position of the ultrasound transducer 12 (in the lateral and/or transverse directions) with respect to the subject. In some embodiments, the correction can be based on the fitting of a geometric model of the arterial path (i.e. the line through the center of the artery) to the peaks (e.g. maximum) of the spatial time profiles, and determining the correction from the deviation of the model and the peaks in the spatial time profiles. The complexity of the geometric model can depend on the number of profiles, with just two profiles, the model is a line, with three profiles, the model is a parabola, etc.

As in the case of the scenario shown in FIG. 4, feedback can be provided to an operator of the ultrasound transducer based on the determined correction to the position. The feedback can be provided in any suitable form using any suitable feedback means in user interface 18.

For example, in some embodiments, the feedback can simply comprise an indication that the orientation and/or position of the ultrasound transducer 12 is not correct, in which case the operator can adjust the orientation and/or position of the ultrasound transducer 12 until the feedback indicates that the orientation and/or orientation is correct. The indication can be a visual, aural and/or tactile indication, or a combination thereof.

In other embodiments, the feedback can be an indication of the translation of the ultrasound transducer 12 with respect to the subject in the lateral and/or transverse directions and/or an indication of the direction of the translation of the ultrasound transducer 12 in the lateral and/or transverse direction that is required to improve the alignment of the probe with the artery (i.e. by reducing the distance between the axis 32 of the ultrasound transducer 12 and the center line of the artery). Again, the indication can be a visual, aural and/or tactile indication, or a combination thereof.

In some embodiments, which can be in addition to or alternatively to the embodiments in which feedback is provided to the operator, the method can further comprise determining a control signal (also referred to herein as a third control signal) for a position actuator 20 for the ultrasound transducer 12 based on the determined correction to the position. The position actuator 20 can then be controlled using the control signal to adjust the position of the ultrasound transducer 12 with respect to the subject in the lateral and/or transverse directions and thereby improve the alignment of the ultrasound transducer 12 with the artery. It will be appreciated that where the actuator 20 can adjust both the angle of the ultrasound transducer 12 and the position of the ultrasound transducer 12, the second and third control signal can be the same signal.

Once the position of the ultrasound transducer 12 has been adjusted, either by the operator in response to the operator feedback or by the position actuator 20, steps 101-105 can be repeated. If in step 105 it is determined that no correction is required to the position of the ultrasound transducer 12, then one or more of the spatial time velocity profiles determined in step 103 can be analyzed to determine the flow velocity of the blood in the aorta 2, and/or any other cardiac parameter that can be derived from the flow velocity of the blood, for example using an aortic flow model.

There is therefore provided a method and apparatus that can provide a reliable measure of flow velocity and thus cardiac output.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of improving a measurement of the flow velocity of blood in a blood vessel of a subject, the method comprising:
   using an ultrasound transducer held at an angle with respect to the subject to emit an ultrasound beam to measure flow velocity at a plurality of depths in a part of a body of the subject;
   forming a respective spatial time velocity profile for the blood vessel from the measured flow velocity for each of the plurality of depths, each spatial time velocity profile being formed from the measured flow velocity at the respective depth; and
   analyzing one or more of the plurality of spatial time velocity profiles to determine a correction to the angle of the ultrasound beam with respect to an axis of the blood vessel of the subject, the correction being based on a difference between a position of a peak in the spatial time velocity profile and a center of the spatial time velocity profile;

determining a control signal for the ultrasound transducer based on the correction with respect to the blood vessel of the subject; and adjusting a position of the ultrasound transducer in a lateral or transverse direction and thereby improving an alignment of the ultrasound transducer with the blood vessel based on the control signal.

2. The method as claimed in claim 1, wherein the method further comprises the step of:

providing feedback to an operator of the ultrasound transducer based on the determined correction to the angle.

3. The method as claimed in claim 1, wherein the method further comprises the steps of:

determining a first control signal for the ultrasound transducer based on the determined correction to the angle; and adjusting the direction of the ultrasound beam emitted by the ultrasound transducer according to the determined first control signal such that the position of the peak in the spatial time velocity profile is in, or nearer to, the center of the spatial time velocity profile.

4. The method as claimed in claim 1, wherein the method further comprises the step of:

determining a second control signal for an orientation actuator for the ultrasound transducer based on the determined correction to the angle, wherein the orientation actuator is capable of adjusting the orientation of the ultrasound transducer with respect to the subject.

5. The method as claimed in claim 1, wherein the method further comprises the step of:

determining a correction to a value of a flow velocity in the spatial time velocity profile based on the determined correction to the angle.

6. The method as claimed in claim 1, wherein the method further comprises the step of:

analyzing the spatial time velocity profiles to determine a correction to the position of the ultrasound transducer with respect to the subject.

7. The method as claimed in claim 6, wherein the method further comprises the step of:

determining a third control signal for a position actuator for the ultrasound transducer based on the determined correction to the position, wherein the position actuator is capable of adjusting the position of the ultrasound transducer with respect to the subject.

8. A computer program product comprising a computer readable medium having computer readable code embodied therein, the computer readable code being configured such that, on execution by a suitable computer or processor, the computer or processor is caused to perform the method of claim 1.

9. An apparatus for measuring flow velocity of blood in a blood vessel of a subject, the apparatus comprising:

an input for receiving signals from an ultrasound transducer that emits an ultrasound beam, the ultrasound transducer being held at an angle with respect to the subject;

a control unit that is configured to:

obtain measurements of flow velocity at different depths in the blood vessel of the subject, wherein the measurements are made using the ultrasound transducer;

form a respective spatial time velocity profile for the blood vessel from the measured flow velocity for each of the plurality of depths, each spatial time velocity profile being formed from the measured flow velocity at the respective depth; and analyze one or more of the plurality of spatial time velocity profiles to determine a correction to the angle of the ultrasound beam with respect to an axis of the blood vessel of the subject, the correction being based on a difference between the position of a peak in the spatial time velocity profile and a center of the spatial time velocity profile; and the control unit further configured to determine a control signal for the ultrasound transducer based on the correction with respect to the blood vessel of the subject, and adjust a position of the ultrasound transducer in a lateral or transverse direction and thereby improving an alignment of the ultrasound transducer with the blood vessel based on the control signal.

10. The apparatus as claimed in claim 9, wherein the control unit is further configured to:

determine a first control signal for the ultrasound transducer based on the determined correction to the angle; and output the first control signal for adjusting the direction of the ultrasound beam emitted by the ultrasound transducer such that the position of the peak in the spatial time velocity profile is in, or nearer to, the center of the spatial time velocity profile.

11. The apparatus as claimed in claim 9, wherein the control unit is further configured to:

determine a second control signal for an orientation actuator for the ultrasound transducer based on the determined correction to the angle, wherein the orientation actuator is capable of adjusting the orientation of the ultrasound transducer with respect to the subject.

12. The apparatus as claimed in claim 9, wherein the control unit is further configured to:

analyze the spatial time velocity profiles to determine a correction to the position of the ultrasound transducer with respect to the subject.

13. The apparatus as claimed in claim 12, wherein the control unit is further configured to:

determine a third control signal for a position actuator for the ultrasound transducer based on the determined correction to the position, wherein the position actuator is capable of adjusting the position of the ultrasound transducer with respect to the subject.

14. The apparatus as claimed in claim 9, wherein the apparatus further comprises the ultrasound transducer.

* * * * *